(12) United States Patent
Tucker

(10) Patent No.: US 7,398,883 B2
(45) Date of Patent: Jul. 15, 2008

(54) BLISTER KIT AND METHOD OF USING SAME

(76) Inventor: Kenneth H. Tucker, 1910 York Ct., Murfreesboro, TN (US) 37129

( * ) Notice: Subject to any disclaimer, the term of this patent is extended or adjusted under 35 U.S.C. 154(b) by 399 days.

(21) Appl. No.: 11/136,178

(22) Filed: May 23, 2005

(65) Prior Publication Data

US 2006/0260974 A1    Nov. 23, 2006

(51) Int. Cl.
*B65D 85/00* (2006.01)

(52) U.S. Cl. .................. 206/570; 206/440; 206/803

(58) Field of Classification Search ............... 206/570, 206/438, 439, 440, 441, 803
See application file for complete search history.

(56) References Cited

U.S. PATENT DOCUMENTS

| | | | | |
|---|---|---|---|---|
| 4,170,300 A | * | 10/1979 | Pick | 206/365 |
| 5,848,700 A | * | 12/1998 | Horn | 206/570 |
| 6,455,752 B1 | * | 9/2002 | Vesey | 602/41 |
| 2002/0104774 A1 | * | 8/2002 | Hammond | 206/570 |
| 2006/0289329 A1 | * | 12/2006 | Miller | 206/570 |

* cited by examiner

*Primary Examiner*—Jacob K Ackun, Jr.
(74) *Attorney, Agent, or Firm*—Jerry R. Potts

(57) ABSTRACT

A blister kit includes a plurality of blister inhibiting coverings of different sizes and shapes, a plurality of blister dressing coverings of different sizes and shapes, a set of instructions for when and where to use individual ones of the coverings, and a container for storing the coverings and the set of instructions.

5 Claims, 2 Drawing Sheets

BLISTER KIT AND METHOD OF USING SAME

STATEMENT REGARDING FEDERALLY SPONSORED RESEARCH OR DEVELOPMENT

Not Applicable

REFERENCE TO MICROFICHE APPENDIX

Not Applicable

CROSS-REFERENCE TO RELATED APPLICATIONS

Not Applicable

BACKGROUND OF THE INVENTION

1. Field of the Invention

This application relates to wound dressing kits. In particular, this invention relates a to a blister kit for helping to inhibit and treat blisters.

2. Background of Prior Art

Outdoorsman, backpackers and athletes are all susceptible to developing severe foot blisters. Therefore there is a need for a new and improved blister dressing kit and blister dressing for treating foot blisters and for helping to reduce further maceration of the healthy surrounding tissue.

BRIEF SUMMARY OF THE INVENTION

In a preferred embodiment of the invention a duct tape blister kit includes a plurality of blister inhibiting coverings of different sizes and shapes, a plurality of blister dressing coverings of different sizes and shapes, a set of instructions for when and where to use individual ones of the coverings, and a container for storing the coverings and the set of instructions.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENT OF THE INVENTION

Figure 1:
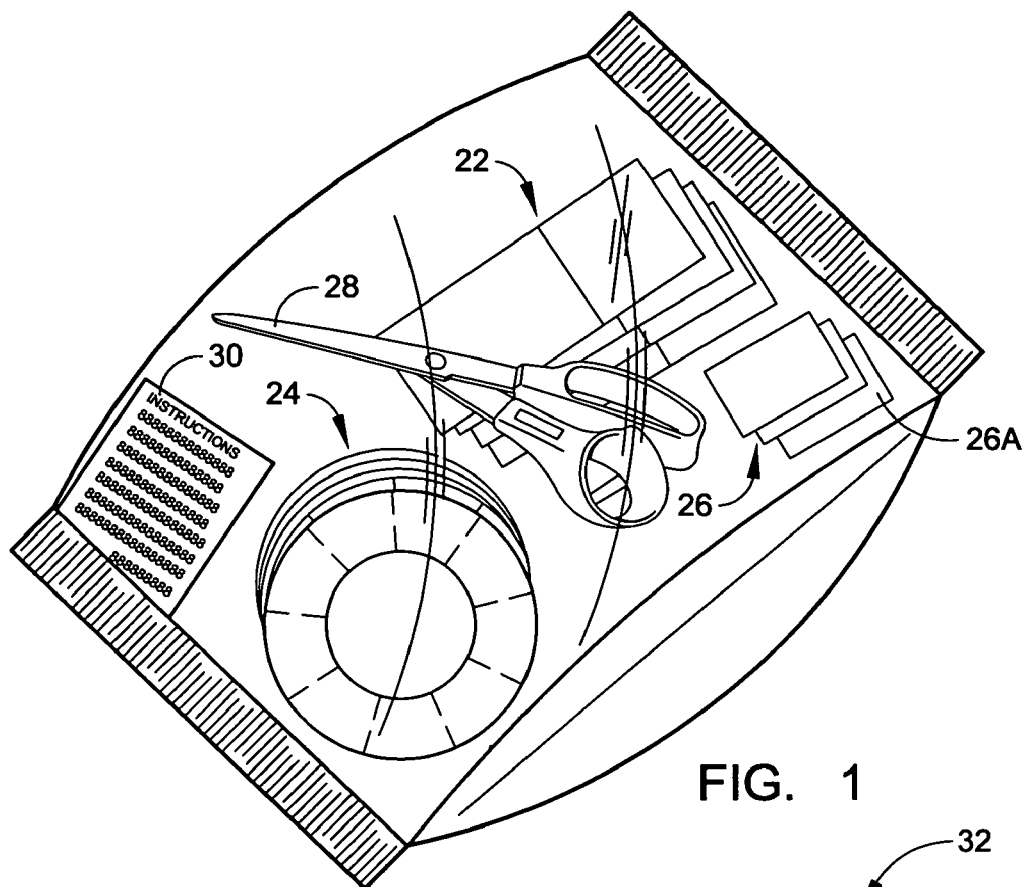
FIG. 1 is a diagrammatic view of a duct tape blister kit, which is constructed in accordance with a preferred embodiment of the present invention.

Referring now to the drawings and more particularly to FIGS. 1-3 and 5, there is illustrated a blister inhibiting kit 10, which is constructed in accordance with the present invention. As best seen in FIG. 1, the blister inhibiting kit 10 is conveniently packaged in a clear carrying bag 12, which enables a user to quickly and easily see the contents of the kit 10.

Before describing the blister inhibiting kit 10 in greater detail, it may be beneficial to briefly consider how a blister is formed. In this regard, a blister occurs when the outer layer of skin receives friction that causes the outer layer to rub against a deeper skin layer. More specifically, as the outer layer is loosened form the deeper skin layer, fluid fills the spaces and cuts off oxygen and nutrients to the outer layer of skin. If the friction continues, the outer layer of skin may rupture, exposing nerve endings that induce pain severe enough to limit or stop the activity that induced the friction. Moreover, if the blister ruptures, the skin loses its natural protective barrier that can lead to a wound infection.

Considering now the blister inhibiting kit 10 in greater detail with reference to FIG. 1, the blister inhibiting kit 10 generally includes a set 22 of blister inhibiting coverings, a set 24 of blister treating coverings, a set 26 of antibiotic ointment packs, a pair of scissors 28 and a sheet of instructions 30.

The set 22 of blister inhibiting coverings are provides to protect different body areas from developing blisters. In this regard, the set 22 of blister inhibiting coverings are configured in different sizes and shapes to accommodate smooth, flat skin areas as well as bony prominences like fingers, heels, elbows, knees and toes. In addition, individual ones of the blister coverings may be cut with the pair of scissors 28 to a customized shape and size should such customizing be necessary.

The set 24 of blister treating coverings are provides to slightly shift pressure and shearing forces from an effected blister site, while simultaneously helping to prevent further traumatization to the blister area and to facilitate reducing further maceration of the healthy tissue surrounding the blister area. As will be explained hereinafter in greater detail, a packet of the antibiotic ointment may be applied to the blister area to help foster a healing process if the blister site has ruptured. Also, like the set 22 of blister inhibiting coverings, the set 24 of blister treating coverings are configured in different sizes and shapes to accommodate smooth, flat skin areas as well as bony prominences like fingers, heels, elbows, knees and toes. In addition, individual ones of the blister treating coverings may be cut with the pair of shears 28 to a customized shape and size should such customizing be necessary.

Figure 2:
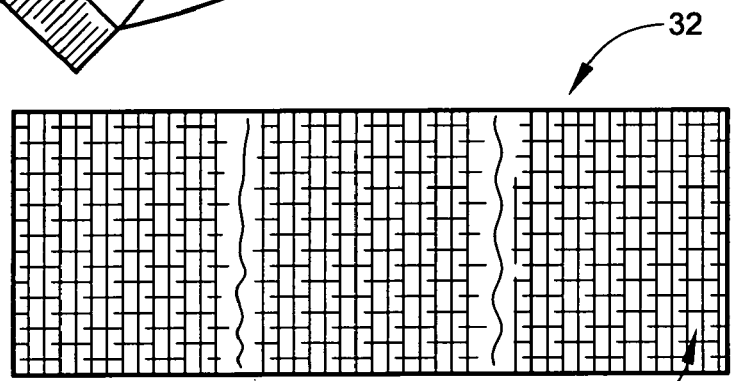
FIG. 2 is an enlarged top plane view of a blister inhibiting covering forming part of the duct tape blister kit of FIG. 1.
Figure 3:
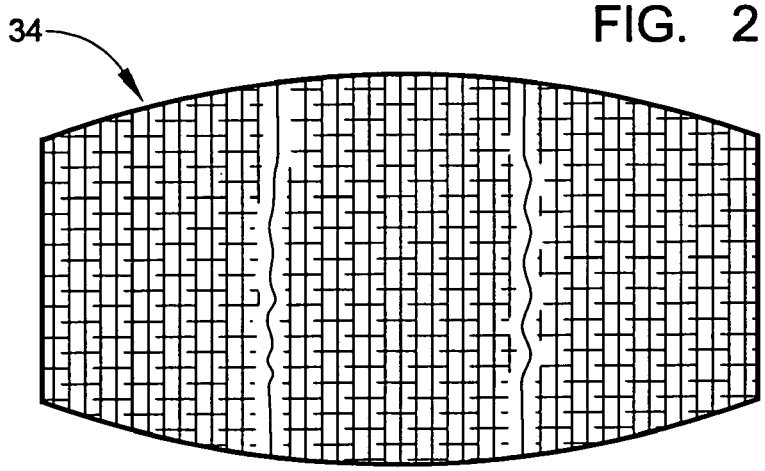
FIG. 3 is an enlarged top plane view of another blister inhibiting covering.
Figure 4:
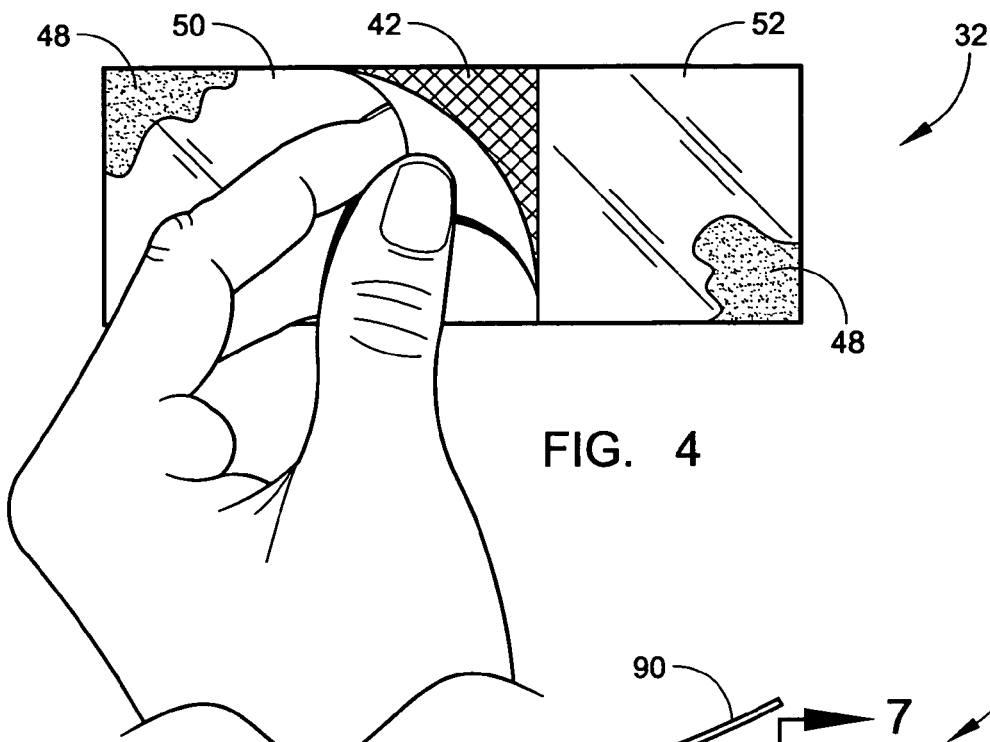
FIG. 4 is side elevational view of the blister inhibiting covering of FIG. 2.

Considering now the set 22 of blister inhibiting coverings in greater detail with reference to FIGS. 1-2, the set 22 of blister inhibiting coverings include individual blister inhibiting coverings, such as a blister inhibiting covering 32 (FIG. 2) and a blister inhibiting covering 34 (FIG. 3). Except for the size and shape of the blister inhibiting coverings 32 and 34, their construction is substantially the same. In this regard, only the blister inhibiting covering 32 will be described hereinafter in greater detail.

Figure 6:
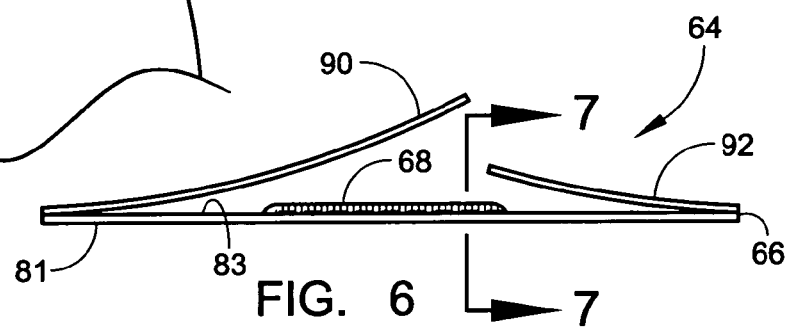
FIG. 6 is side elevational view of a blister dressing covering constructed in accordance with a preferred embodiment of the present invention.
Figure 5:
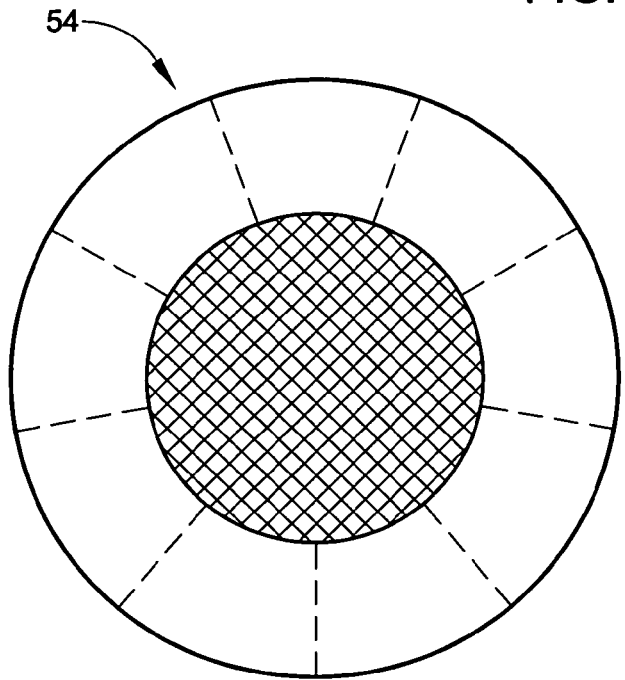
FIG. 5 is an enlarged top plane view of a blister dressing covering forming part of the duct tape blister kit of FIG. 1.

Considering now the blister inhibiting covering 32 in greater detail with reference to FIGS. 2 and 6, the blister inhibiting covering 32 generally includes an inhibitor layer of mole skin 42 for helping to reduce skin shearing in response to a rubbing action and an anchoring layer of duct tape 44 which is affixed to the inhibitor layer 42 for securing the inhibitor layer of mole skin 42 over an area of "at risk" skin tissue. The anchoring layer of duct tape 44 includes a non-adhesive fabric like upper surface indicated generally at 46 and a sticky gummy adhesive surface indicated generally at 48. The combination of the mole skin 42 with duct tape 44 greatly increases retaining the mole skin 42 in a covering relationship relative to the at risk skin site, which in turn significantly reduces shearing at this site as well. This combination of mole skin 42 and duct tape 44, even in a moist condition, significantly reduces a stage I pressure area (also called a hot spot) from becoming a stage II or stage III pressure sore (blister).

In order to protect the mole skin 42 and the sticky gummy adhesive surface 48 of the duct tape 44 until the blister inhibiting covering 32 is ready for use, a pair of protective peel coverings 50 and 52 respectively cover the mole skin 42 and the adhesive surface 48 of the duct tape 44. As best seen in FIG. 6, when a user is ready to apply the blister inhibiting covering 32 to an at risk skin area, the user simply pinches a corner of one of the peel covering, such as the peel covering 50 and pulls it away from the mole skin 42 and the adhesive surface 48. The user then repeats this process removing the peel covering 52 and then applies the mole skin 42 directly over the at risk site, allowing the uncovered adhesive surface 48 to fix the mole skin 42 in place.

Figure 7:
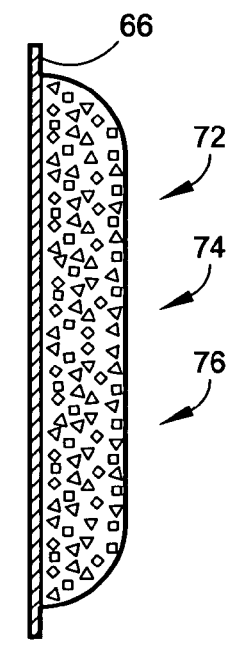
FIG. 7 is a cross sectional view of the blister dressing covering of FIG. 6 taken substantially along section line 7-7.

Considering now the set 24 of blister treating coverings in greater detail with reference to FIGS. 1 and 5-7, the set 22 of blister inhibiting coverings include individual blister inhibiting coverings, such as a blister treating covering 54 (FIG. 5) and a blister treating covering 64 (FIG. 7). Except for the size and shape of the blister inhibiting coverings 54 and 64, their construction is substantially the same. In this regard, only the blister inhibiting covering 64 will be described hereinafter in greater detail.

Considering now the blister treating covering 64 in greater detail with reference to FIGS. 6-7, the blister treating covering generally includes an anchoring layer of duct tape 66 which is affixed to a treatment layer of polyurethane foam 68. The treatment layer of polyurethane foam 68 functions to accomplish several beneficial effects: it helps wick away moisture discharged from the blister site, it helps reduce external pressure exerted on the blister site, and it helps protect the traumatized skin at the blister site.

In order to promote the above-mentioned beneficial effects and in order to help foster rapid healing of the pressure sore, the polyurethane foam 68 is impregnated with a mild cleansing agent 72, such as an F-68 surfactant, a moisturizer 74, such as glycerin, and a starch co-polymer 76.

The cleansing agent 72 is activated by moisture (fluid released from the blister site) and is gradually released onto the blister area to help decrease surface friction that traumatized the skin and the underlying tissue. The moisturizer 74 on the other hand, keeps the polyurethane foam 68 from adhering to the traumatized skin or wound surface, thereby significantly decreasing discomfort and pain that could otherwise be experienced by the user. The starch co-polymer 76 accelerates the wound healing process by providing a moist wound environment that helps facilitate the concentration of the body's natural growth factors and nutrients at the wound site.

Also, in order to help prevent infection and to promote the rapid healing of the wound, the user may apply a unit dosage of antibiotic ointment 26A to the traumatized skin surface area prior to covering the wound with the blister treating covering 64.

When impregnating the polyurethane foam 68, it has been found that the foam 68 should preferably be at least 90% to 99% free of the surfactant 72, 90% to 99% free of the glycerin and 90% to 99% free of the co-polymer starch. More preferably the foam 68 should preferably be at least 95% to 99% free of the surfactant 72, 95% to 99% free of the glycerin and 95% to 99% free of the co-polymer starch. Most preferably the foam 68 should preferably be at least 99% free of the surfactant 72, 99% free of the glycerin and 99% free of the co-polymer starch.

The anchoring layer of duct tape 66 includes a non-adhesive fabric like upper surface indicated generally at 81 and a sticky gummy adhesive surface indicated generally at 83. The combination of the impregnated polyurethane foam membrane 68 with duct tape 66 greatly increases retaining the polyurethane foam 66 in a covering relationship relative to the wound site, which in turn, helps to accelerate the healing process.

In order to protect the mole skin 42 and the sticky gummy adhesive surface 83 of the duct tape 66 until the blister treating covering 642 is ready for use, a pair of protective peel coverings 90 and 92 respectively cover the polyurethane foam member 68 and the adhesive surface 83 of the duct tape 66. As best seen in FIG. 6, when a user is ready to apply the blister treating covering 64 to a wound area, the user simply pinches a corner of one of the peel covering, such as the peel covering 90 and pulls it away from the polyurethane foam member 68 and the adhesive surface 83. The user then repeats this process removing the peel covering 92 and then applies the impregnated polyurethane foam membrane 68 directly over the blister site, allowing the uncovered adhesive surface 83 to fix the polyurethane foam membrane 68 in place at the wound site.

Although the preferred embodiments of the present invention have been described as having a uniquely formulated dressing, it is nevertheless contemplated that other less effective dressings may be utilized to impregnate the polyurethane foam membrane 68. For example, the following other dressings are contemplated: silver-coated antimicrobial barrier dressings; dressing composed of ester of hyaluronic acid; thin film dressings which are semi-permeable membrane dressing permeable to oxygen and water vapor; hydrocolloid dressing that are moldable wafer dressings which may interact with wound exudates to form a moist gel which protects the wound bed; alginates dressings which are products made of seaweed that promote body fluids combining with the alginate to form a gel; hydrogels/gel dressings that are non-adhesive, single polymer formulations that are useful for the treatment of granulating wounds and which can lower the temperature of the wound thus reducing inflammation and providing pain relief; foam and absorptive dressing which absorb wound exudates and conform to the wound surface thus obliterating dead space; combination dressings of inert materials that conforms to the wound surface and help obliterate dead space, maintain a moist would surface and allow a moderate amount of wound exudates to pass through the dressing for absorption by a secondary dressing or an absorptive layer in the primary dressing; collagen dressings; and barriers and lotions that are skin protectants that allow for moisture-vapor transport and protect skin from maceration. While particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A blister kit, comprising:
    a plurality of blister inhibiting coverings of different sizes and shapes;

a plurality of blister dressing coverings of different sizes and shapes;

a set of instructions for when and where to use individual ones of said blister inhibiting coverings and for when and where to use individual ones of said blister dressing coverings; and a container for storing said plurality of blister inhibiting coverings, said plurality of blister dressing coverings and said set of instructions; and wherein each individual one of said plurality of blister inhibiting coverings includes:

an inhibitor layer for helping to reduce skin shearing in response to a rubbing action; and an anchoring aver affixed to said inhibitor layer for securing said inhibitor layer over an area of at risk skin tissue; and wherein said inhibitor layer is a layer of moleskin or a layer of polyurethane foam; and wherein said layer of polyurethane foam is impregnated with an F-68 surfactant for helping to reduce surface friction on said area of at risk skin tissue; and wherein said polyurethane foam is at least 99% free of said F-68 surfactant.

2. The blister kit according to claim 1, further comprising:

a pair of scissors for cutting and customizing the size and shape of at least an individual one of said plurality of blister inhibiting coverings; and wherein said layer of polyurethane foam is further impregnated with a starch co-polymer for helping to wick away moisture from said area of at risk skin tissue.

3. The blister kit according to claim 2, said pair of scissors for cutting and customizing the size and shape of at least an individual one of said plurality of blister dressing coverings; and wherein said polyurethane foam is at least 99% free of said starch co-polymer.

4. The blister kit according to claim 3, wherein said layer of polyurethane foam is further impregnated with an antibiotic ointment for helping skin healing.

5. The blister kit according to claim 4, wherein each individual one of said plurality of blister dressing coverings includes:

a moisture wicking, pressure redirecting layer of polyurethane foam;

a moisture releasing agent disposed within said layer of polyurethane foam for helping to prevent said layer of polyurethane foam from adhering to a blister wound area;

a cleansing agent disposed within said layer of polyurethane foam for helping to reduce surface tension between said polyurethane foam and said blister wound area; and an anchoring layer affixed to said layer of polyurethane foam for securing said layer over a blister wound area of skin tissue; and wherein said anchoring layer is a layer of duct tape; and wherein one half of the bottom surface of said duct tape and one half of the inhibitor layer is covered by a removable peel sheet; and wherein another one half of the bottom surface of said duct tape and another one half of the inhibitor layer is covered by another removable peel sheet.

* * * * *